United States Patent [19]

Schloman, Jr.

[11] 4,436,853

[45] Mar. 13, 1984

[54] PHENOL-MELAMINE RESINS FOR IMPROVING RUBBER TO METAL ADHESION

[75] Inventor: William W. Schloman, Jr., Stow, Ohio

[73] Assignee: The Goodyear Tire & Rubber Company, Akron, Ohio

[21] Appl. No.: 409,790

[22] Filed: Aug. 20, 1982

[51] Int. Cl.$^3$ .................. C08L 7/00; C08L 9/00; C08L 9/02; C08L 9/06

[52] U.S. Cl. .................. 524/91; 524/87; 524/95; 524/100; 528/211

[58] Field of Search .................. 528/211; 524/87, 95, 524/100, 91

[56] References Cited

U.S. PATENT DOCUMENTS

| | | | |
|---|---|---|---|
| 3,293,212 | 12/1966 | Power et al. | 528/211 |
| 3,476,701 | 11/1969 | Aldred et al. | 528/211 |
| 3,904,623 | 9/1975 | Shay et al. | 528/211 |
| 4,338,263 | 7/1982 | Elmer | 524/100 |

Primary Examiner—Lester L. Lee
Attorney, Agent, or Firm—H. C. Young, Jr.; D. J. Hudak

[57] ABSTRACT

A metal to rubber adhesion promoter comprising the reaction product of a phenol and a substituted melamine, said phenol being

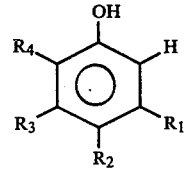

wherein $R_1$ through $R_4$ are selected from the group consisting of hydrogen, cyclic and acyclic alkyl groups having from 1 to 10 carbon atoms, and a substituted melamine having the formula

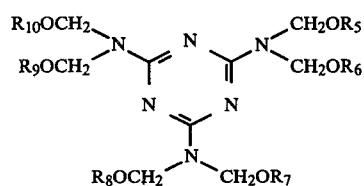

where $R_5$ through $R_{10}$ may be the same or different and are selected from the group consisting of alkyl groups having from 1 to 5 carbon atoms. The reaction product is a resin and is added to the rubber compound prior to cure. The adhesion promoter is useful in the making of tires having steel belts and in other reinforced rubber articles.

13 Claims, No Drawings

PHENOL-MELAMINE RESINS FOR IMPROVING RUBBER TO METAL ADHESION

TECHNICAL FIELD

The invention herein lies in the art of metal to rubber adhesion. Specifically, the invention teaches the use of a class of rubber compounding ingredients which may be used to improve the adhesion of rubber to a metal surface such as brass coated steel wire. Typical applications include the use of rubber coated wire in the construction of passenger and truck tires.

BACKGROUND ART

Various reinforcing materials have long been used to increase the strength of rubber articles, including tires, hoses, and the like. Metallic wire, and in particular brass coated steel wire is commonly used as reinforcement. A primary requirement for effective reinforcement is that the reinforcing material remain tightly bonded to the rubber. Good adhesion is difficult to achieve where, as in the case of a tire, the article is subject to continuous flexing and exposure to high temperatures during use. High initial adhesion may be obtained by providing good mechanical contact between the rubber and the wire during cure but, upon aging and use of the article, the bond is often weakened or is lost completely, resulting in premature failure. To prevent this, adhesion promoters are often used which can maintain a high level of adhesion between the rubber and metal. The promoters are commonly added to the rubber compounding recipe prior to cure. The present invention provides for a novel wire adhesion promoter which is the reaction product of a substituted melamine and a phenol or alkyl substituted phenol. The product, a resin, is then neutralized, purified and added to the uncured rubber during compounding in a conventional manner.

U.S. Pat. No. 3,517,722 to Endter, et al, discloses rubber modified with a resin formed in situ from the reaction of a methylene donor and a methylene acceptor. The donor includes a substituted melamine while the acceptor may be m-aminophenol (MAP) or a resorcinol. This patent differs from the present invention in that the reaction in the former is carried out in situ, has no neutralization or purification step, and a phenol or alkyl substituted phenol is not used.

U.S. Pat. Nos. 4,189,421 and 3,904,623 to Shay, et al, refer to the use of the reaction product of a phenolic and a triazine compound as a crosslinking agent in powder coatings, for example, polyesters. There is no teaching or suggestion of the use of such a reaction product as an adhesion promoter between rubber and metal. Thus, these patents are not pertinent.

DISCLOSURE OF INVENTION

It is an aspect of the present invention to provide a promoter for rubber to metal adhesion.

It is another aspect of the present invention to provide a promotor, as above, which can be manufactured using readily available starting materials.

It is yet another aspect of the present invention to provide a promoter, as above, which is a resin formed prior to being compounded in a rubber recipe.

Still another aspect of the present invention is to provide a promoter, as above, which can be used to promote adhesion of rubber to metal wire in a tire or in other industrial rubber products.

Yet another aspect of the present invention is to provide a promoter, as above, which is non-fuming.

These aspects and others which will become apparent as the detailed description proceeds, are achieved by: an adhesion promoter for rubber to metal adhesion, comprising the reaction product of: a phenol having the formula

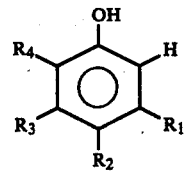

where $R_1$, $R_2$, $R_3$ and $R_4$ may be the same or different and are selected from the group consisting of hydrogen and $C_1$ to $C_{10}$ acyclic and cyclic alkyl radicals; and a substituted melamine having the formula

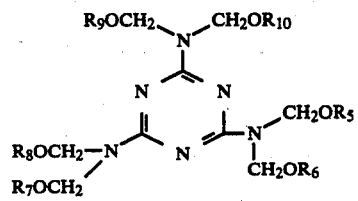

where $R_5$, $R_6$, $R_7$, $R_8$, $R_9$ and $R_{10}$ are selected from the group consisting of $C_1$ to $C_5$ alkyl radicals; wherein said reaction product is added to a rubber compounding recipe in an amount between 1 and 8 parts per 100 parts by weight rubber.

BEST MODE FOR CARRYING OUT THE INVENTION

The compounds of the invention comprise the reaction products of phenol or substituted phenols and substituted melamines. In general useful phenols include those having the formula:

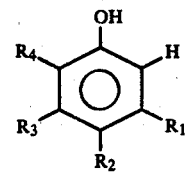

where $R_1$, $R_2$, $R_3$ and $R_4$, are the same or different and are selected from the group consisting of —H, and acyclic and cyclic alkyl radicals having from 1 to 10 carbon atoms with between 1 and 4 preferred. Substituted melamines have the general formula:

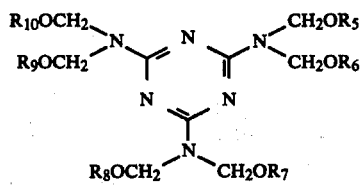

where $R_5$, $R_6$, $R_7$, $R_8$, $R_9$ and $R_{10}$ are selected from the group consisting of alkyl radicals having from 1 to 5 carbon atoms with methyl or ethyl preferred.

The reaction is carried out in the presence of an acidic catalyst such as p-toluene sulfonic acid hydrate, the condensation products of the reaction being resins and the corresponding alcohol by-product. Following completion of the reaction, the resins are neutralized to remove catalyst residue by the use of either a solid alkali compound such as $CaCO_3$, or $Ca(OH)_2$ or by an aqueous solution of $Na_2CO_3$ or NaOH. The resin is then isolated from the neutralizing agent by well known techniques such as a phase separation with an immiscible organic solvent if an aqueous alkali solution is used. When solid alkali such as lime is used, the resin may be washed with an organic solvent and then filtered. Suitable organic solvents include toluene, benzene, tetrahydrofuran (THF), acetone, and the like. The pH of the neutralizing agent is not critical, as long as neutralization is effected. The neutralized, isolated resin should have a softening point above about 70° C. as measured using ASTM E28-67. Softening points below this temperature make handling difficult.

The resins can be used in various rubber compounding recipes to enhance the adhesion of metal, usually in the form of a cable or wire, to the rubber. The specific rubber compounds which may utilize the promoter are limited only to the requirement of being sulfur curable. Thus, recipes may contain natural or synthetic cis 1,4-polyisoprene, styrene-butadiene, nitrile rubber, butyl rubber, the various neoprene rubbers, and/or the ethylene-propylene terpolymers (EPDM) which contain unsaturated hydrocarbon groups. Other rubbers not specifically recited may also be used. The compounding recipes, in addition to containing one or more rubbers, sulfur and the adhesion promoter of the invention, may contain various other well known rubber compounding ingredients such as antioxidants, carbon black, processing oils and the like in conventional amounts as is known in the art.

The examples given below illustrate both the preparation and use of the resins in a typical rubber compounding recipe. Of the various substituted melamines, preferred is hexamethoxymethylmelamine or HMMM, available commercially under various trade names, for example, CYREZ 963, manufactured by American Cyanimid. Preferred phenols include p-cresol, 4-(p-menthyl)phenol and p-isopropylphenol.

The reaction is catalyzed, as above, by various well known compounds including p-toluene sulfonic acid hydrate, oxalic acid, and the like, and is carried out at a temperature which is at least as high as the boiling point of the alcohol by-product. For example, the reaction between HMMM and p-isopropylphenol yields methanol as a by-product, so that, in order to remove the methanol as it is formed through distillation, the reaction mixture must be maintained at at least the boiling point of methanol, i.e., 65° C. As methanol represents the lowest boiling alcohol, 65° C. is thus the minimum reaction temperature regardless of the substituted melamine used. A preferred reaction temperature ranges between about 85° and 100° C. but the temperature can be as high as 150° C.

The number average molecular weights of the resins have been found to be higher than what would be expected from a simple condensation reaction. Table V is illustrative of the molecular weights obtained when HMMM is reacted with p-cresol and 4-(p-menthyl)-phenol, having the softening points indicated. These molecular weights suggest that various oligomerization reactions occur, with dimerization being predominant.

It is emphasized, however, that while oligomers are present, primary reaction products include the substituted benzoxazenes, that is:

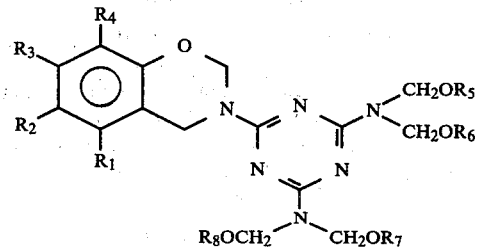

where the various R's are defined above. Note that if the groups depending from the melamine nitrogen atoms, that is, $R_5$ through $R_{10}$ are not identical, mixture of benzoxazenes will result. Similarly, if the two groups on each nitrogen are different, the by-product alcohol will be a mixture.

The physical properties of the resins may be varied by manipulation of the starting materials and the processing conditions. Specifically, if one or more of these substitutent groups $R_1$ through $R_4$ are higher alkyl that is 8 to 10 carbon atoms, the softening point is higher than where the substitutents have only between 1 and 3 carbon atoms. Higher softening points can also be obtained by varying the molar ratio of the hydroxybenzene to the substituted melamine. The higher the ratio, that is, the greater the amount of hydroxybenzene in relation to the melamine, the higher the softening point. For example, a molar ratio of 2:1 gives a softening point of 128° C. when HMMM is reacted with p-isopropylphenol while a ratio of 1:1 yields a softening point of 75° C. for the HMMM/p-isopropylphenol reaction. Other melamine and/or hydroxybenzenes have a simlar relationship between ratio and softening point. Lastly, the softening point can be varied by the use of a steam sparge treatment of the resin, wherein the steam is at a temperature of between 150° C. and 325° C., and preferably between 200° C. and 250° C. The steam sparge, which is introduced after the resin has been purified and isolated, is continued until approximately 2 parts by weight of distillate is obtained for every part by weight of resin. The distillate, in addition to containing condensed steam, is composed of low molecular weight reaction products and possibly unreacted melamine and/or hydroxybenzene.

The amount of the resins which are used in a rubber compound is between about 1 and 8 parts per 100 parts by weight of rubber and preferably between 2 and 6 parts. Improvement in adhesion can be characterized by the maintenance of high levels of adhesion during accelerated rubber compound aging at elevated temperatures, which is illustrated in Table II, below. The amount of resin which is used in the rubber compound has an effect on the cure rate and compound hardness, as shown by Tables III and IV respectively.

All of the Tables II through IV compare the use of the adhesion promoter, at various phr levels, to a control compound having no adhesion promoter. The rubber recipe used to obtain the data in the Tables can be seen in Table I. In compounding the rubber stock in accordance with the formulation in Table I, a master batch consisting of ingredients 1 through 4 was made in a Banbury, with final mixing carried out in a mill at about 110° C. The resulting master batch was then cooled and ingredients 5 and 6 were added in a Banbury at a temperature of about 70° C. The balance of the ingredients were added in a mill at about 45° C. Wire cable was embedded in rubber specimens prepared following the method described in U.S. Pat. No. 4,095,465 to Rongone, et al, issued June 20, 1978. The specimens were vulcanized at 150° C. from about 25 to 55 minutes, the optimum cure times having been determined by means of a Monsanto Oscillating Disc Curemeter (ASTM method D2084-81). The force necessary to pull the adhered cable free from the rubber, the adhesion value in newtons, was determined, following the method in Rongone, et al, after immersing the rubber specimens in water at a temperature of about 90° C. for the lengths of times specified in Table II.

As can be seen with reference to Table II, the 56 day adhesion of all rubber compounds utilizing the adhesion promoter is far superior to the control. A general trend of increasing adhesion is also observed as the amount of the adhesion promoter increases in the rubber compounds. The control illustrates the characteristic high initial adhesion which deteriorates with time as is commonly observed with rubber compounds having no adhesion promoter.

The cure data summarized in Table III shows that use of the adhesion promoter retards the cure slightly. Table IV illustrates the variations and hardness observed wherein resins of selected examples are used. Note that the rubber compound hardness is not significantly increased when low amounts of the resin are present. Shore A hardness is seen to increase at progressively higher loadings of low-ratio resins but not increase significantly using high-ratio or high-softening resins. Generally, a ratio of hydroxybenzene to melamine of less than about 2.0:1 is preferred, while Shore A hardness should be about 75 and preferably above about 78.

The following examples illustrate the preparation of the various resins used to generate the data in the Tables. The wire cable used in the tests had a $3 \times 0.20 + 6 \times 0.38$ construction and is commonly used in making the plies of a pneumatic tire. The surface of each strand of steel wire is coated with brass (an alloy of 69% copper and 31% zinc plus or minus 4%) at the rate of 6.5 grams of brasss per kilogram of steel plus or minus 1.5 grams. The wire cable is thereafter treated with the rubber made and compounded according to the formula in Table I.

EXAMPLE 1

A mixture of 32.2 parts of p-cresol and 115.8 parts of HMMM was heated to 90° C. The fused mixture was treated at 85°–95° C. with 3.0 parts of p-toluene-sulfonic acid hydrate, reaction conditions being maintained while a nitrogen stream was passed through the reaction mixture by means of a sparge tube so as to facilitate the distillation of methanol. After 17.9 parts of methanol had been collected, the reaction was neutralized with a mixture of 6.0 parts of lime and 0.8 parts of water. The mixture was diluted with 65 parts of toluene, then filtered prior to charging into a flask for stripping. Desolventization with a nitrogen sparge to 200° C. afforded 218.6 parts of a yellow resin having a ring and ball softening point (ASTM Method E28-67) of 66° C.

EXAMPLE 2

A solution of 11.4 parts of the resin described in Example 1 in 65 parts of toluene was desolventized with a nitrogen sparge to 200° C., followed by a steam sparge at 200°–210° C. until 218.4 parts of aqueous distillate had been collected. By this means, 107.0 parts of an amber resin having a ring and ball softening point of 84° C. was obtained. The molecular weight ($M_n$) of the resin was 811.

EXAMPLE 3

A mixture containing 390.0 parts of HMMM, 136.2 parts of 4-(p-menthyl) phenol, and 118.0 parts of dipentene dimers was treated with 10.0 parts of p-toluenesulfonic acid hydrate at 90°–100° C. following the procedure in Example 1. After 43.0 parts of methanol had been collected, the reaction was neutralized with 30.0 parts of lime and 2.0 parts of water. The mixture was diluted with 175 parts of toluene prior to filtration and desolventization. The desolventized resin was steam sparged at 200°–250° C. to afford, after 770.0 parts of aqueous distillate had been collected, 471.0 parts of a tan resin having a ring and ball softening point of 102° C. The molecular weight ($M_n$) of the resin was 878.

The dipentene dimers were initially charged in the reaction mixture with the phenol and represent an inert impurity present in commercially available 4-(p-menthyl)phenol. Consisting primarily of limonene, the dimers are removed in the steam sparge.

EXAMPLE 4

A mixture containing 40.9 parts of p-isopropylphenol and 117.1 parts of HMMM was treated with 3.0 parts of p-toluenesulfonic acid at 85°–95° C. following the procedure in Example 1. After 15.3 parts of methanol had been collected, the mixture was diluted with 130 parts of toluene and neutralized by treatment with a solution of 3.0 parts of sodium carbonate in 9.0 parts of water. After further dilution with 90 parts of toluene, the resin solution was washed three times with 50 parts of water. Desolventization of the resin solution to 250° C. afforded 129.2 parts of a tan resin having a ring and ball softening point of 64.5° C.

EXAMPLE 5

Following the procedure in Example 2, 122.4 parts of the resin described in Example 4 was stripped by means of a steam sparge to afford, after 250.0 parts of aqueous distillate had been collected, 118.3 parts of a tan resin having a ring and ball softening point of 75° C.

EXAMPLE 6

A mixture of 61.6 parts of p-isopropyphenol and 88.3 parts of HMMM was treated with 3.0 parts of p-toluenesulfonic acid at 85°–95° C. following the procedure in Example 1. After 24.2 parts of methanol had been collected, the viscous mixture was diluted with 175 parts of toluene and neutralized following the procedure in Example 4. Desolventization of the resin solution to 200° C. afforded 103.9 parts of a tan resin having a ring and ball softening point of 128° C.

TABLE I

| | ADHESION TEST RECIPE | |
|---|---|---|
| | Ingredients | Parts by Weight |
| 1. | Cis 1,4-polyisoprene | 100 |
| 2. | Carbon black | 57 |
| 3. | Antioxidant (mixture of diamines) | 0.8 |
| 4. | Stearic Acid | 2 |
| 5. | Zinc oxide | 8 |
| 6. | Silica | 8 |

TABLE I-continued

ADHESION TEST RECIPE

| Ingredients | Parts by Weight |
|---|---|
| 7. Sulfenamide | 0.8 |
| 8. Sulfur | 4 |
| 9. Resin | Variable |

TABLE II

WIRE PULL-OUT FORCE (P), HOT WATER AGING AT 90° C.

| | | P, N* | | | | | |
|---|---|---|---|---|---|---|---|
| Resin Example No. | Resin Wgt., phr. | 0 | 7 | 14 | 28 | 42 | 56 Days |
| Control | 0 | 425 | 444 | 402 | 410 | 379 | 286 |
| 2 | 1 | 466 | 542 | 536 | 525 | 523 | 441 |
| | 2 | 483 | 545 | 535 | 514 | 523 | 474 |
| | 4 | 503 | 625 | 587 | 614 | 576 | 555 |
| | 6 | 492 | 569 | 569 | 579 | 580 | 563 |
| 3 | 2 | 449 | 506 | 505 | 492 | 458 | 409 |
| | 4 | 471 | 496 | 530 | 503 | 492 | 477 |
| | 6 | 459 | 543 | 542 | 506 | 510 | 510 |
| 5 | 1 | 454 | 539 | 528 | 513 | 447 | 380 |
| | 2 | 440 | 546 | 520 | 509 | 476 | 437 |
| | 4 | 473 | 550 | 530 | 539 | 532 | 480 |
| | 6 | 473 | 563 | 567 | 556 | 542 | 533 |
| 6 | 1 | 429 | 516 | 492 | 489 | 483 | 302 |
| | 2 | 442 | 508 | 498 | 500 | 518 | 276 |
| | 4 | 427 | 475 | 493 | 494 | 474 | 415 |
| | 6 | 405 | 492 | 487 | 516 | 452 | 452 |

*As measured according to Rongone, et al, U.S. Pat. No. 4,095,465.

TABLE III

CURE DATA 300° F.

| Resin Example No. | Resin Wgt., phr | $t_s^2$ min.* | t(90) min.* |
|---|---|---|---|
| Control | 0 | 6 | 26 |
| 2 | 1 | 6 | 31 |
| | 2 | 6.5 | 37 |
| | 4 | 6.5 | 49 |
| | 6 | 6.5 | 55 |
| 3 | 2 | 6 | 33 |
| | 4 | 6.5 | 41 |
| | 6 | 7.5 | 47 |
| 5 | 1 | 6 | 31 |
| | 2 | 6.5 | 35 |
| | 4 | 6 | 44 |
| | 6 | 6.5 | 54 |
| 6 | 1 | 6 | 28 |
| | 2 | 6 | 30 |
| | 4 | 6 | 33 |
| | 6 | 7 | 38 |

*ASTM D 2084-81 using an oscillating disc Curemeter.

TABLE IV

HARDNESS DATA

| Resin Example No. | Wgt., phr | Shore A* |
|---|---|---|
| Control | 0 | 74 |
| 2 | 1 | 77 |
| | 2 | 78 |
| | 4 | 81 |
| | 6 | 82 |
| 5 | 1 | 76 |
| | 2 | 78 |
| | 4 | 78 |
| | 6 | 80 |
| 6 | 1 | 75 |
| | 2 | 75 |
| | 4 | 74 |
| | 6 | 75 |

*ASTM D676, Shore A Durometer.

TABLE V

PHYSICAL CHARACTERISTICS OF SELECTED MELAMINE-PHENOLIC RESINS

| Resin From Example | Starting Phenol | Softening Point, °C. | $\overline{M}_n$** |
|---|---|---|---|
| 1 | p-cresol | 66 | — |
| 2 | p-cresol | 88* | 811 |
| 3 | 4-(p-methyl)phenol | 102 | 878 |

*After 200-210° C. steam sparge of the resin of example 1.
**Number average molecular weight.

The invention finds utility in various areas of rubber to wire adhesion, and in particular to wire coat stocks which are used in the manufacture of steel belts in radial car, truck and off-the-road tires. Other applications include V belts and similar industrial rubber products.

The resins of the invention, unlike some prior art adhesion promoters, do not fume significantly due to the removal of volatile components during the steam sparge described above. Thus, considerable cost savings can be utilized and reduced expenditures for worker protection, particularly in labor intensive industries such as tire manufacture. Further, use of hydroxybenzenes as starting materials is advantageous in that such compounds are frequently found in the waste streams of various chemical processes and thus cost is low.

While in accordance with the Patent Statutes, only the best mode and preferred embodiments have been disclosed, it is to be understood that the invention is not limited thereto or thereby. Therefore, for a fuller understanding of the true scope of the invention, reference should be made to the following appended claims.

What is claimed is:

1. A rubber compound, including an adhesion promoter for rubber to metal adhesion, comprising:
the adhesion promoter consisting of the reaction product of a phenol and a substituted melamine, said phenol having the formula

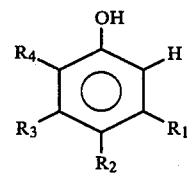

where $R_1$, $R_2$, $R_3$ and $R_4$ may be the same or different and are selected from the group consisting of hydrogen and $C_1$ to $C_{10}$ acyclic and cyclic alkyl radicals; and
a substituted melamine having the formula

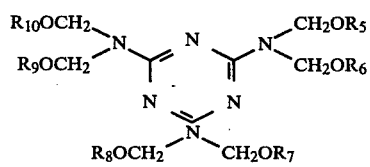

$R_5$, $R_6$, $R_7$, $R_8$, $R_9$ and $R_{10}$ are selected from the group consisting of $C_1$ to $C_5$ alkyl radicals; wherein said reaction product is added to a rubber compounding recipe in an amount between 1 and 8 parts per 100 parts by weight rubber; and
wherein the rubber is a sulfur curable elastomer.

2. A rubber compound according to claim 1, wherein said reaction product has a softening point greater than 70° C. as measured by ASTM E28-67.

3. A rubber compound according to claim 2, wherein said product increases the adhesion of rubber to metal compared to a control having no adhesion promoter as measured by a 56 day accelerated aging test.

4. A rubber compound according to claim 3, wherein the mole ratio of said phenol to said substituted melamine in the reaction is from about 1.0:1.0 to about 2.0:1.0; and
wherein said phenol is p-isopropylphenol and said substituted melamine is hexamethoxymethylmelamine.

5. A rubber compound according to claim 4, wherein said promoter is non-fuming.

6. A rubber compound according to claim 5, wherein said promoter is used to promote the adhesion between rubber and brass or bronze coated wire, and wherein said rubber is used in the manufacture of a tire.

7. A rubber compound, comprising: a rubber to metal adhesion promoter comprising one or a mixture of compounds selected from the group consisting of

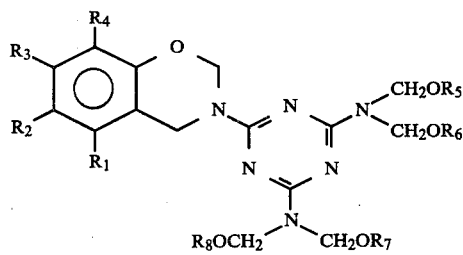

where $R_1$, $R_2$, $R_3$ and $R_4$ may be the same or different and are selected from the group consisting of —H and $C_1$ to $C_{10}$ alkyl groups, and where $R_5$, $R_6$, $R_7$ and $R_8$ may be the same or different and are selected from the group consisting of $C_1$ to $C_5$ alkyl groups; and
wherein the rubber is a sulfur curable elastomer.

8. A rubber compound according to claim 7, wherein said promoter is used in an amount between 1 and 8 parts per 100 parts by weight rubber and wherein said promoter increases the adhesion of rubber to metal compared to a control having no adhesion promoter, as measured by a 56 day accelerated aging test.

9. A rubber compound according to claim 8, wherein the softening point of said promoter is greater than about 70° C.

10. A rubber compound according to claim 9, wherein said promoter is

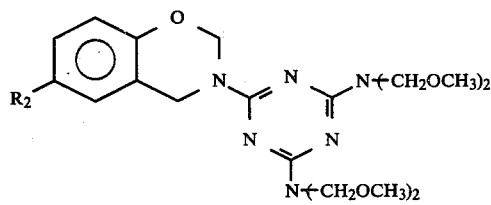

where $R_2$ is selected from the group consisting of p-isopropyl and methyl and wherein said promoter is present in said rubber compounding recipe in an amount between 2 and 6 parts per 100 parts by weight rubber.

11. A rubber compound according to claim 10, wherein said promoter is non-fuming and is used to promote the adhesion between rubber and brass or bronze coated wire; and
wherein said rubber is used in the manufacture of a tire.

12. A rubber compound according to claim 6, wherein said sulfur curable elastomer is selected from the group consisting of natural and synthetic cis 1,4 polyisoprene, styrenebutadiene, nitrile, butyl, neoprene, ethylene-propylene terpolymers containing unsaturated hydrocarbon groups, and combinations thereof.

13. A rubber compound according to claim 11, wherein said sulfur curable elastomer is selected from the group consisting of natural and synthetic cis 1,4 polyisoprene, styrenebutadiene, nitrile, butyl, neoprene, ethylene-propylene terpolymers containing unsaturated hydrocarbon groups, and combinations thereof.

* * * * *